United States Patent
Xu et al.

(10) Patent No.: US 12,387,358 B2
(45) Date of Patent: Aug. 12, 2025

(54) APPARATUS AND METHOD FOR CONFIGURING SCAN PARAMETERS

(71) Applicant: GE Precision Healthcare LLC, Wauwatosa, WI (US)

(72) Inventors: Yanran Xu, Beijing (CN); Bingjie Zhao, Beijing (CN); Hsieh Jiang, Waukesha, WI (US); Ziyu Liu, Beijing (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 501 days.

(21) Appl. No.: 17/727,151

(22) Filed: Apr. 22, 2022

(65) Prior Publication Data
US 2022/0319030 A1   Oct. 6, 2022

(30) Foreign Application Priority Data
Mar. 31, 2021  (CN) .......................... 202110348381.2

(51) Int. Cl.
*G06T 7/62* (2017.01)
*G06T 7/10* (2017.01)
*G06T 7/50* (2017.01)

(52) U.S. Cl.
CPC .................. *G06T 7/62* (2017.01); *G06T 7/10* (2017.01); *G06T 7/50* (2017.01); *G06T 2207/10024* (2013.01); *G06T 2207/10028* (2013.01)

(58) Field of Classification Search
CPC .... G06T 7/62; G06T 7/10; G06T 7/50; G06T 2207/10024; G06T 2207/10028; G06T 7/13; G06T 2207/10012; G06T 2207/10081; A61B 6/544; A61B 6/481; A61B 6/545; A61B 6/032; G06N 3/08
See application file for complete search history.

(56) References Cited

U.S. PATENT DOCUMENTS

| | | | |
|---|---|---|---|
| 2014/0241570 A1* | 8/2014 | Onen | G06F 3/017 |
| | | | 382/103 |
| 2017/0103510 A1* | 4/2017 | Wang | G06T 7/33 |
| 2018/0071452 A1* | 3/2018 | Sharma | A61M 5/007 |
| 2019/0357844 A1* | 11/2019 | Raupach | A61B 5/0077 |
| 2020/0412940 A1* | 12/2020 | Huang | G06V 10/82 |
| 2022/0277835 A1* | 9/2022 | Senegas | G16H 30/40 |

* cited by examiner

*Primary Examiner* — Roy M Punnoose

(57) ABSTRACT

An apparatus and method for configuring scan parameters for an imaging system are described. The method for configuring scan parameters includes acquiring an RGB image and a depth image of a scan object, computing physical parameters of the scan object according to the RGB image and the depth image of the scan object, and configuring, according to the physical parameters, scan parameters for scanning the scan object. In this way, the scan parameters for scanning the scan object can be automatically configured, which improves the efficiency and standardization of a scan process. Moreover, an appropriate configuration of scan parameters can further avoid rescanning and poor-quality scout images resulting from manual errors. An example apparatus that may be used to perform the method includes an acquisition unit for acquiring the RGB image, a first computation unit for computing the physical parameters, and a configuration unit for configuring the scan parameters.

14 Claims, 5 Drawing Sheets

APPARATUS AND METHOD FOR CONFIGURING SCAN PARAMETERS

CROSS-REFERENCE TO RELATED APPLICATIONS

This application claims priority to Chinese Patent Application No. 202110348381.2, filed on Mar. 31, 2021, the disclosure of which is incorporated herein by reference in its entirety.

BACKGROUND

In some computed tomography (CT) scan scenarios, such as a contrast scan and a large-sized patient scan, the scan quality or image quality largely depends on the patient size and the configuration of related scan parameters.

Generally, before a scan, an operator needs to manually input information such as the height and weight of a patient, and manually configure appropriate scan parameters accordingly.

It should be noted that the above background introduction is only for the purpose of clearly and completely describing the technical solutions of the present application and facilitating understanding by a person skilled in the art.

SUMMARY

In some cases, information, such as the height and weight of a patient, is generally given by the patient themselves. However, in other cases, the patient does not know the accurate information about their height, weight, and the like. For example, special populations such as children may not know information about their height, weight, and the like. On the other hand, in some cases, the patient may not be able to tell their height and weight; for example, in the case of serious injury, the patient may be unconscious and thus unable to speak. In addition, even if the patient can accurately provide information such as the height and weight, in some cases, an operator may configure corresponding scan parameters incorrectly due to lack of experience.

Regarding at least one of the above technical problems, provided in the embodiments of the present application are an apparatus and method for configuring scan parameters of a medical imaging system. It is expected that scan parameters related to the patient size can be automatically configured, so as to improve the efficiency and standardization of a scan process.

According to an aspect of the embodiments of the present application, an apparatus for configuring scan parameters is provide. The apparatus includes an acquisition unit for acquiring an RGB image and a depth image of a scan object from a three-dimensional camera, a first computation unit for computing physical parameters of the scan object according to the RGB image and the depth image of the scan object, and a configuration unit for configuring, according to the physical parameters of the scan object, scan parameters for scanning the scan object.

In some embodiments, the first computation unit includes a segmentation unit for segmenting the RGB image by means of a deep learning neural network to obtain two-dimensional profile information of the scan object, a mapping unit for mapping the two-dimensional profile information to the depth image so as to obtain upper surface information of the scan object, and a second computation unit for computing physical parameters of the scan object according to the upper surface information of the scan object.

In some embodiments, the first computation unit further includes an estimation unit for estimating lower surface information of the scan object according to information of a supporting member supporting the scan object. The second computation unit computes the physical parameters of the scan object according to the upper surface information and the lower surface information of the scan object.

In some embodiments, the information of the supporting member includes at least one of a shape, size, and configured height of the supporting member.

In some embodiments, the apparatus further includes a preprocessing unit for performing preprocessing on the RBG image, the preprocessing comprising at least one of denoising, normalization, cropping, and scaling. The first computation unit computes the physical parameters of the scan object according to the preprocessed RBG image and the depth image of the scan object.

In some embodiments, the physical parameters of the scan object include at least one of the following: a length of the scan object, a thickness of the scan object, a width of the scan object, a volume of the scan object, and a weight of the scan object.

In some embodiments, the scan parameters include at least one of the following: a body mass index (BMI), a dosage and a flow rate of a contrast medium, a scan voltage and current, an indication of whether the scan object is beyond the scan field of vision, a medication administration range, a height of the supporting member, and an indication of whether the scan object is a special population.

In some embodiments, the scan object is the entire body or a portion of the scan object.

According to another aspect of the embodiments of the present application, a method for configuring scan parameters is provided. The method includes acquiring an RGB image and a depth image of a scan object from a three-dimensional camera, computing physical parameters of the scan object according to the RGB image and the depth image of the scan object, and configuring, according to the physical parameters of the scan object, scan parameters for scanning the scan object.

According to another aspect of the embodiments of the present application, an electronic device is provided, including a memory and a processor, the memory storing a computer program, and the processor being configured to execute the computer program so as to implement the method for configuring scan parameters as described above.

One of the beneficial effects of the embodiments of the present application is as follows: according to the embodiments of the present application, the scan parameters for scanning the scan object can be automatically configured, so as to improve the efficiency and standardization of a scan process. Moreover, an appropriate configuration of the scan parameters can further avoid rescanning and poor-quality scout images resulting from manual errors.

Referring to the description and drawings below, specific implementations of the embodiments of the present application are disclosed in detail, indicating the method in which the principle of the embodiments of the present application may be employed. It should be understood that the implementations of the present application are not hereby limited in scope. Within the scope of the spirit and terms of the appended claims, the implementations of the present application comprise many changes, modifications, and equivalents.

BRIEF DESCRIPTION OF THE DRAWINGS

The drawings included herein are used to provide a further understanding of the embodiments of the present application, constituting a portion of the description, and are used for illustrating the implementations of the present application and explaining the principle of the present application together with textual description. The drawings in the following description are merely some embodiments of the present application, and those of ordinary skill in the art can obtain other implementations according to these drawings without the exercise of inventive effort. In the drawings.

DETAILED DESCRIPTION

Figure 1:
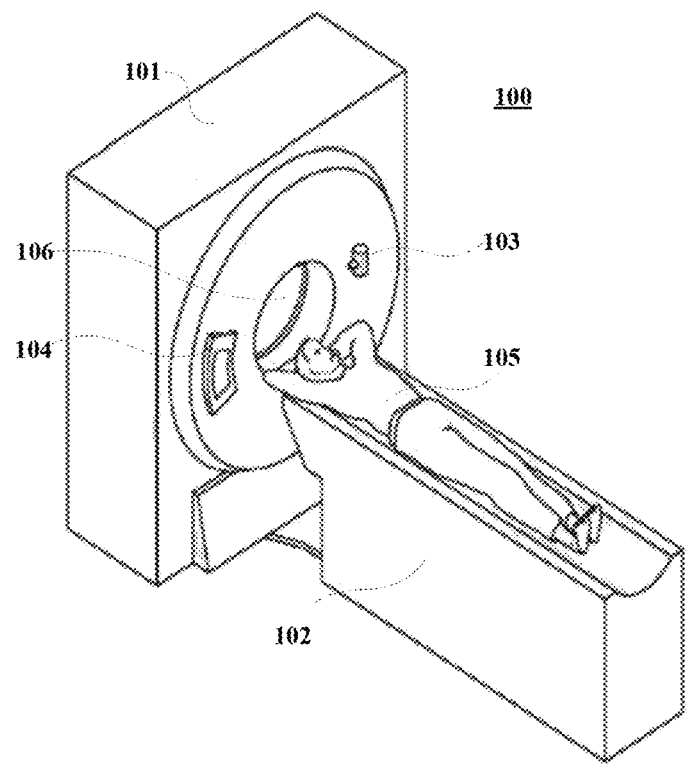
FIG. 1 is a schematic diagram of a CT imaging device according to an embodiment of the present application.

Referring to the drawings, the foregoing and other features of the embodiments of the present application will become apparent due to the following description. In the description and the drawings, specific implementations of the present application are specifically disclosed, indicating some implementations that can employ the principles of the embodiments of the present application. It should be understood that the present application is not limited to the embodiments described, and rather, the embodiments of the present application include all modifications, variations, and equivalents within the scope of the appended claims.

In the embodiments of the present application, the terms "first", "second", etc. are used to distinguish different elements, but do not represent a spatial arrangement or temporal order etc. of these elements, and these elements should not be limited by these terms. The term "and/or" includes any one of and all combinations of one or more of the associated listed terms. The terms "comprise", "include", "have", etc. refer to the presence of described features, elements, components, or assemblies, but do not exclude the presence or addition of one or more other features, elements, components, or assemblies.

In the embodiments of the present application, the singular forms "a", "the", etc. include plural forms, and should be broadly construed as "a type of" or "a class of" rather than limited to the meaning of "one". Furthermore, the term "said" should be construed as including both the singular and plural forms, unless otherwise specified in the context. In addition, the term "according to" should be construed as "at least in part according to . . . ", and the term "based on" should be construed as "at least in part based on . . . ", unless otherwise specified in the context.

The features described and/or illustrated for one implementation may be used in one or more other implementations in the same or similar manner, combined with features in other implementations, or replace features in other implementations. The term "include/comprise" when used herein refers to the presence of features, integrated components, steps, or assemblies, but does not preclude the presence or addition of one or more other features, integrated components, steps, or assemblies.

The apparatus for acquiring medical image data described herein can be applied to various medical imaging modalities, including but not limited to a computed tomography (CT) device, a magnetic resonance imaging (MRI) device, a C-arm imaging device, a positron emission computed tomography (PET) device, a single photon emission computed tomography scanning (SPECT) device, or any other appropriate medical imaging device.

A system for acquiring medical image data may include the aforementioned medical imaging device, may also include a separate computer device connected to the medical imaging device, and may further include a computer device connected to the Internet cloud. The computer device is connected via the Internet to a medical imaging device or a memory for storing medical images. An imaging method may be independently or jointly implemented by the aforementioned medical imaging device, the computer device connected to the medical imaging device, and the computer device connected to the Internet cloud.

Exemplarily, the embodiments of the present application are described below in conjunction with an X-ray computed tomography (CT) device. Those skilled in the art could understand that the embodiments of the present application can also be applied to other medical imaging devices.

FIG. 1 is a schematic diagram of a CT imaging device according to an embodiment of the present application, and schematically illustrates a CT imaging device 100. As shown in FIG. 1, the CT imaging device 100 includes a gantry 101 and a patient table 102. The gantry 101 has an X-ray source 103, and the X-ray source 103 projects an X-ray beam towards a detector assembly or a collimator 104 on an opposite side of the gantry 101. A test object 105 can lie on the patient table 102 and be moved into a gantry opening 106 along with the patient table 102. Medical image data of the test object 105 can be acquired by means of scanning performed by the X-ray source 103.

Figure 2:
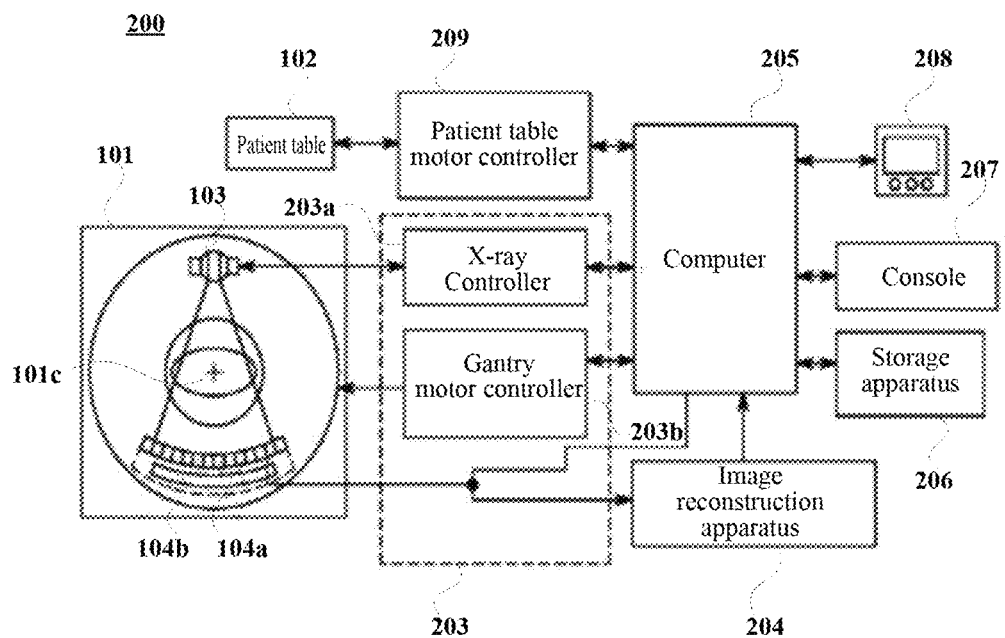
FIG. 2 is a schematic diagram of a CT imaging system according to an embodiment of the present application.

FIG. 2 is a schematic diagram of a CT imaging system according to an embodiment of the present application, and schematically illustrates a block diagram of a CT imaging system 200. As shown in FIG. 2, the detector assembly 104 includes a plurality of detector units 104a and a data acquisition system (DAS) 104b. The plurality of detector units 104a sense the projected X-ray passing through the test object 105.

The DAS 104b converts, according to the sensing performed by the detector units 104a, collected information into projection data for subsequent processing. During the scanning in which X-ray projection data is acquired, the gantry 101 and components mounted thereon rotate about a rotation center 101c.

The rotation of the gantry 101 and the operation of the X-ray source 103 are controlled by a control mechanism 203 of the CT imaging system 200. The control mechanism 203 includes an X-ray controller 203a for providing power and a timing signal to the X-ray source 103, and a gantry motor controller 203b for controlling the rotation speed and position of the gantry 101. An image reconstruction apparatus 204 receives the projection data from the DAS 104b and performs image reconstruction. A reconstructed image is transmitted as an input to a computer 205, and the computer 205 stores the image in a mass storage apparatus 206.

The computer 205 further receives an instruction and scan parameters from an operator through a console 207. The console 207 has a certain kind of operator interface, such as a keyboard, a mouse, a voice-activated controller, or any other appropriate input device. An associated display 208 allows the operator to observe the reconstructed image and other data from the computer 205. The instruction and parameters provided by the operator are used by the computer 205 to provide control signals and information to the DAS 104b, the X-ray controller 203a, and the gantry motor controller 203b. Additionally, the computer 205 operates a patient table motor controller 209 for controlling the patient table 102 so as to position the test object 105 and the gantry 101. In particular, the patient table 102 enables the entirety or part of the test object 105 to move through the gantry opening 106 of FIG. 1.

The device and system for acquiring medical image data (which may also be referred to as medical images or medical image data) according to the embodiments of the present application are schematically described above, but the present application is not limited thereto. The medical imaging device may be a CT device, an MM device, a PET device, a SPECT device, or any other appropriate imaging device. A storage device may be located within the medical imaging device, in a server external to the medical imaging device, in an independent medical image storage system (such as a picture archiving and communication system (PACS)), and/or in a remote cloud storage system.

Moreover, a local medical imaging workstation can be provided for the medical imaging device, that is, the medical imaging workstation is disposed adjacent to the medical imaging device, and both of them can be located in a scan room, an imaging department, or the same hospital. A medical image cloud platform analysis system can be located far away from the medical imaging device, for example, it can be disposed in a cloud that communicates with the medical imaging device.

As an example, after a medical institution completes an imaging scan by means of the medical imaging device, scan data is stored in the storage device. The medical imaging workstation can directly read the scan data and perform image processing by means of a processor thereof. As another example, the medical image cloud platform analysis system can read a medical image in the storage device by means of remote communication to provide "software as a service (SAAS)." The SAAS can exist between hospitals, between a hospital and an image center, or between a hospital and a third-party online diagnosis and treatment service provider.

The medical image scanning is schematically illustrated above, and the embodiments of the present application are described in detail below with reference to the drawings.

Figure 3:
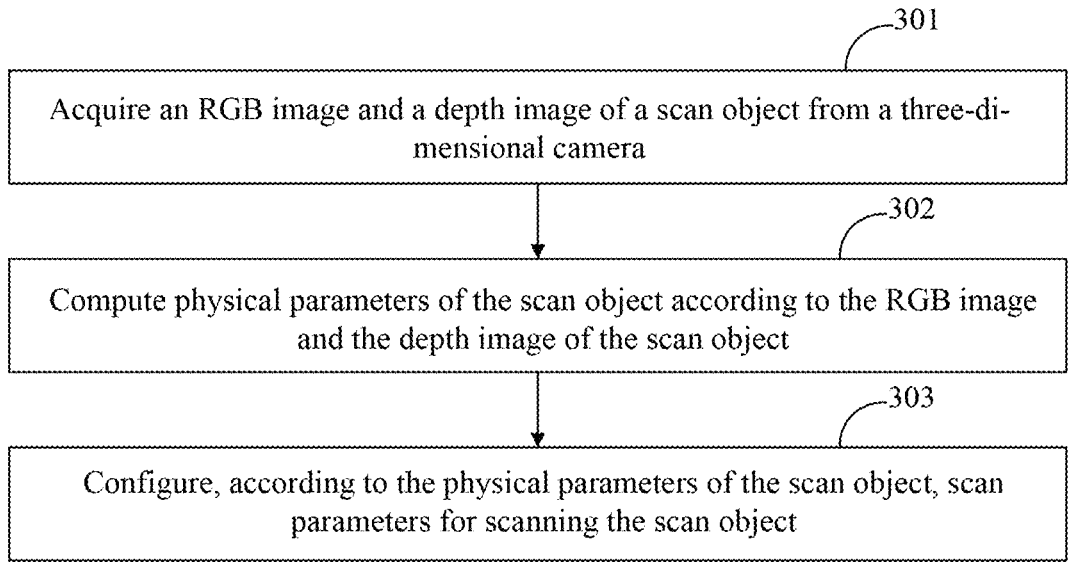
FIG. 3 is a schematic diagram of a method for configuring scan parameters according to an embodiment of the present application.

Provided in a first embodiment of the present application is a method for configuring scan parameters. FIG. 3 is a schematic diagram of the method for configuring scan parameters according to this embodiment of the present application. As shown in FIG. 3, the method includes: at 301, acquiring an RGB image and a depth image of a scan object from a three-dimensional camera; at 302, computing physical parameters of the scan object according to the RGB image and the depth image of the scan object; and at 303, configuring, according to the physical parameters of the scan object, scan parameters for scanning the scan object.

It should be noted that FIG. 3 only schematically illustrates this embodiment of the present application, but the present application is not limited thereto. For example, the execution order of the operations may be adjusted appropriately. In addition, some other operations may be added, or some of the operations may be skipped. Those skilled in the art could make appropriate variations according to the above content, and the present application is not limited to the description of FIG. 3.

In step 301, the three-dimensional camera can be disposed at any position where the RGB image and depth image of the scan object can be acquired, for example, on a ceiling in the scenario shown in FIG. 1, or at other appropriate positions. The RGB image and the depth image of the scan object can be obtained by the three-dimensional camera. The RGB image is a two-dimensional image, and each pixel on the RGB image is represented by red, green, and blue color components. The depth image is a three-dimensional image, and each pixel on the depth image represents an actual distance between the three-dimensional camera and a captured object. Depending on the variations of depth cameras, the meaning represented by each pixel on the depth image slightly differs from one another. For example, each pixel on the depth image may also represent a vertical distance from a captured object to a camera plane, etc. For details, reference may be made to the related art, and the description is omitted herein. Generally, the RGB image and the depth image are registered, so there is a correspondence between pixels of the two images. For definitions of the RGB image and the depth image, reference may be made to the related art, and the description is omitted herein.

In steps 302 and 303, the physical parameters of the scan object are computed according to the RGB image and the depth image of the scan object without depending on information told by the patient, and the scan parameters for scanning the scan object are automatically configured according to the automatically acquired physical parameters without needing to manually configure the scan parameters, thereby improving the efficiency and standardization of a scan process, and avoiding rescanning and poor-quality scout images resulting from manual errors.

Figure 4:
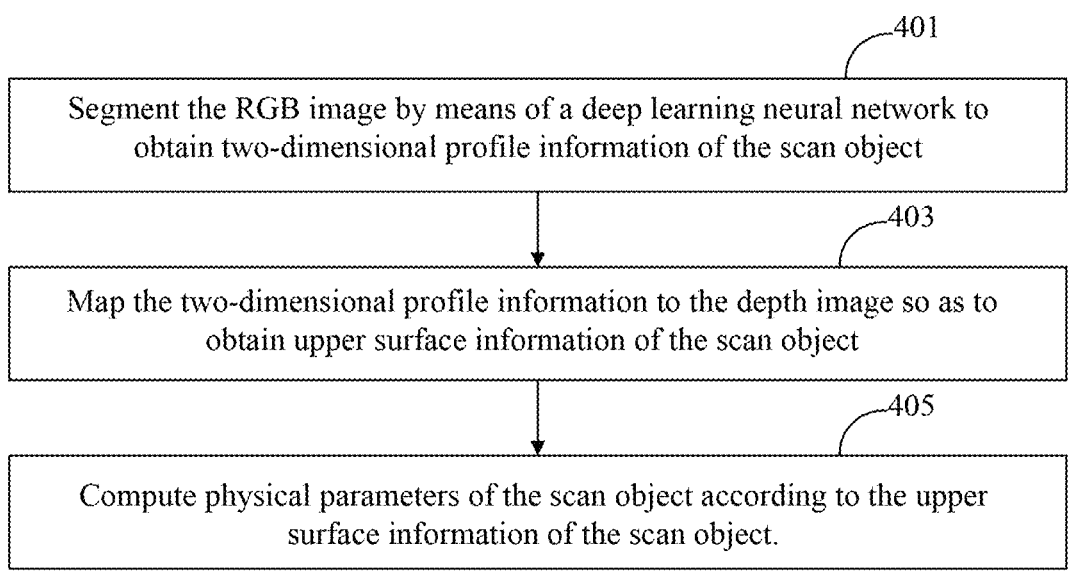
FIG. 4 is a schematic diagram of an example of computing physical parameters of a scan object.

In some embodiments, operation 302 may be implemented using the method shown in FIG. 4. As shown in FIG. 4, the method includes: at 401, segmenting the RGB image by means of a deep learning neural network to obtain two-dimensional profile information of the scan object; at 403, mapping the two-dimensional profile information to the depth image so as to obtain upper surface information of the scan object; and at 405, computing the physical parameters of the scan object according to the upper surface information of the scan object.

In step 401, there are no restrictions to the type of the deep learning neural network and the segmentation method. For example, the RGB image can be segmented by means of a mask-region-convolutional neural network (Mask-R-CNN) to obtain the two-dimensional profile information of the scan object.

Figure 5:
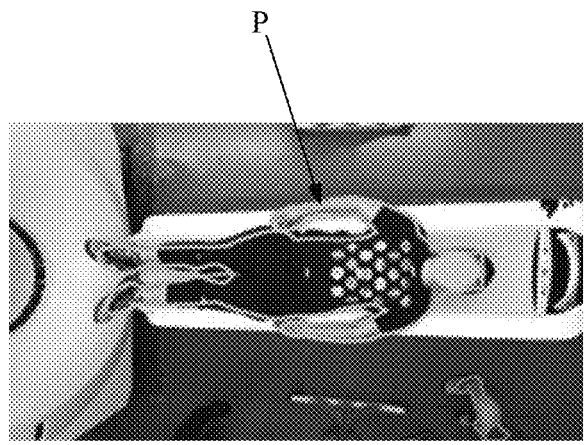
FIG. 5 is a schematic diagram of an example of an RGB image of the scan object.

FIG. 5 is a schematic diagram of an example of the RGB image of the scan object (human body) acquired by the three-dimensional camera. As shown in FIG. 5, the RGB image can be segmented by means of a deep learning neural network, including but not limited to a Mask-R-CNN, so as to obtain two-dimensional profile information P of the scan object (human body).

In step 403, since there is a correspondence between the pixels of the RGB image and the depth image, upper surface information of the scan object can be obtained by mapping the two-dimensional profile information of the scan object from the RGB image to the depth image. The upper surface information of the scan object includes the three-dimensional coordinates of each point on the upper surface of the scan object.

Figure 6:
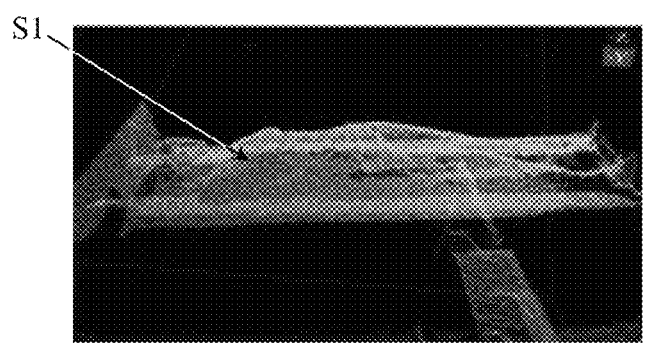
FIG. 6 is a schematic diagram of an example of upper surface information of the scan object.

FIG. 6 is a schematic diagram of an example showing the step of mapping the two-dimensional profile information obtained in step 401 to the depth image, so as to obtain upper surface information of the scan object. As shown in FIG. 6, upper surface information Si is three-dimensional, and includes the three-dimensional coordinates of each point on the upper surface of the human body (scan object).

In step 405, the physical parameters of the scan object are computed according to the upper surface information of the scan object. The present application is not restricted to a specific computation method, and different computation methods may be adopted depending on the various physical parameters required.

In this embodiment of the present application, the scan object is not limited to the entire human body, but may also be a portion of the human body, such as a certain part of the human body. In addition, in this embodiment of the present application, the scan object is not limited to the human body, and may also be an animal body or other organisms, or a portion of an animal body or other organisms, and the like.

Physical parameters vary with scan objects. Taking a scan object being the entire human body as an example, in some embodiments, the physical parameters of the scan object include at least one of the following: a length of the scan object; a thickness of the scan object; a width of the scan object; a volume of the scan object; and a weight of the scan object.

The length of the scan object represents the height of the human body, and the length, thickness, and width of the scan object can be used to compute the volume or weight of the human body.

The above physical parameters of the scan object are merely examples for illustration. Depending on the different types of scan objects, or according to different scanning needs, other physical parameters may be computed according to the upper surface information of the scan object acquired in step 403, and the description is omitted herein.

Figure 7:
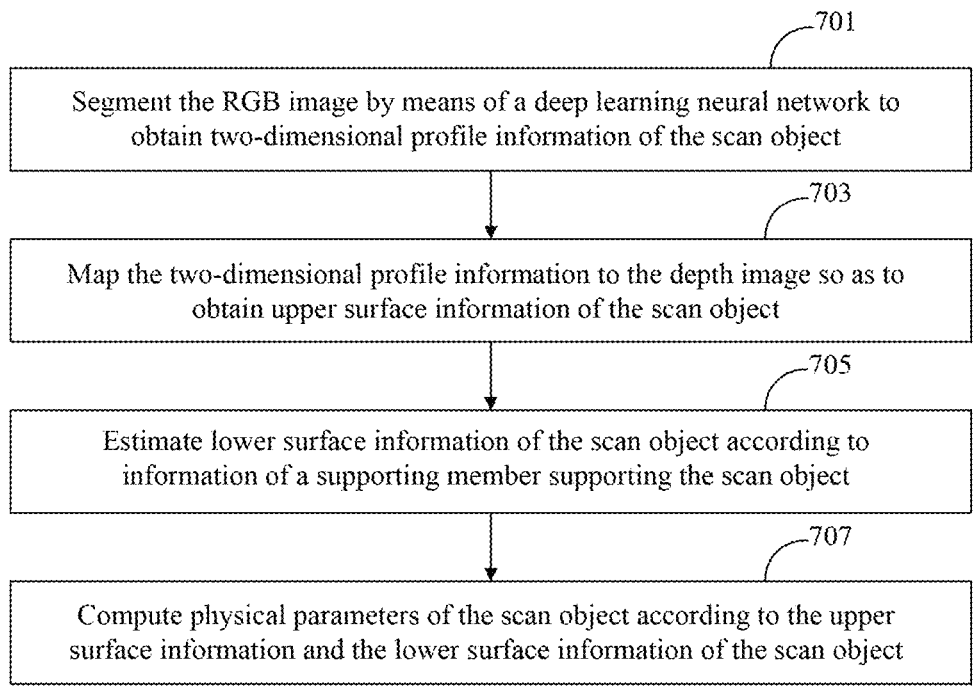
FIG. 7 is a schematic diagram of another example of computing the physical parameters of the scan object.

In some embodiments, operation 302 may be implemented using the method shown in FIG. 7. As shown in FIG. 7, the method includes: at 701, segmenting the RGB image by means of a deep learning neural network to obtain two-dimensional profile information of the scan object; at 703, mapping the two-dimensional profile information to the depth image so as to obtain upper surface information of the scan object; at 705, estimating lower surface information of the scan object according to information of a supporting member supporting the scan object; and at 707, computing the physical parameters of the scan object according to the upper surface information and the lower surface information of the scan object.

The processing in steps 701 and 703 is the same as that in steps 401 and 403 of FIG. 4, and the description is omitted herein.

In step 705, the lower surface information of the scan object can be estimated according to the information of the supporting member supporting the scan object.

In the above embodiment, as shown in FIG. 1 and FIG. 5, during a CT scan, the scan object generally lies on the patient table, and therefore the lower surface information of the scan object cannot be acquired from the RGB image and/or depth image collected by the three-dimensional camera. In this embodiment of the present application, the information of the supporting member supporting the scan object is used as a-priori information to estimate the lower surface information of the scan object, thereby providing a further reference for computing the physical parameters of the scan object.

In the above embodiment, the supporting member is, for example, a patient table, and may also be other supporting members. The information of the supporting member includes a shape, size, and height of the supporting member, but the present application is not limited thereto. The information of the supporting member may also include a length, width, and depression depth of the supporting member.

In step 707, the physical parameters of the scan object are computed with reference to the upper surface information and the lower surface information of the scan object, so that the physical parameters are more accurate.

In step 303, after the physical parameters of the scan object are acquired in step 302 (such as the length, thickness, width, volume, weight, etc. of the scan object), scan parameters for scanning the scan object can be configured according to the physical parameters.

In some embodiments, the scan parameters include at least one of the following: a body mass index (BMI); a dosage and a flow rate of a contrast medium; a scan voltage and current; an indication of whether the scan object is beyond the scan field of vision; a medication administration range; a height of the supporting member; and an indication of whether the scan object is a special population.

The body mass index, the indication of whether the scan object is beyond the scan field of vision, the height of the supporting member, and the indication of whether the scan object is a special population (such as children) can be directly acquired by converting the above physical parameters. The dosage and flow rate of the contrast medium, the scan voltage and current, and the medication administration range, etc. can be obtained by presetting scan parameter values corresponding to different physical parameter ranges and then comparing the obtained one or more physical parameters with the ranges, so as to obtain corresponding scan parameters.

For example, different weight ranges are preset, and are configured to correspond to different dosages and flow rates of the contrast medium. After the weight of the scan object is obtained according to the physical parameters, the weight is compared with the different weight ranges, and a dosage and a flow rate of the contrast medium corresponding to a weight range within which the weight falls are used as the dosage and flow rate of the contrast medium for the scan object.

The above scan parameters are merely examples, and depending on scanning needs, other clinically required scan parameters may also be configured according to the acquired upper surface information or the acquired upper surface information and lower surface information of the scan object.

In this embodiment of the present application, in order to make the two-dimensional profile information of the scan object more accurate, the RGB image acquired by the three-dimensional camera may be preprocessed. In step 302, the physical parameters of the scan object are computed according to the preprocessed RBG image and the depth image of the scan object.

The preprocessing method is not restricted in the above embodiment. The preprocessing can be one or more of denoising, normalization, cropping, and scaling. For specific implementation methods of the denoising, normalization, cropping, and scaling, reference may be made to the related art and there are no restrictions thereto in the present application.

The above embodiments merely provide illustrative description of the embodiments of the present application. However, the present application is not limited thereto, and appropriate variations may be made on the basis of the above embodiments. For example, each of the above embodiments may be used independently, or one or more of the above embodiments may be combined.

According to this embodiment of the present application, the scan parameters for scanning the scan object can be automatically configured, so as to improve the efficiency and standardization of a scan process. Moreover, an appropriate configuration of the scan parameters can further avoid rescanning and poor-quality scout images resulting from manual errors.

Provided in another embodiment of the present application is an apparatus for configuring scan parameters, and the content the same as that of the embodiment of the first aspect is not repeated herein.

Figure 8:
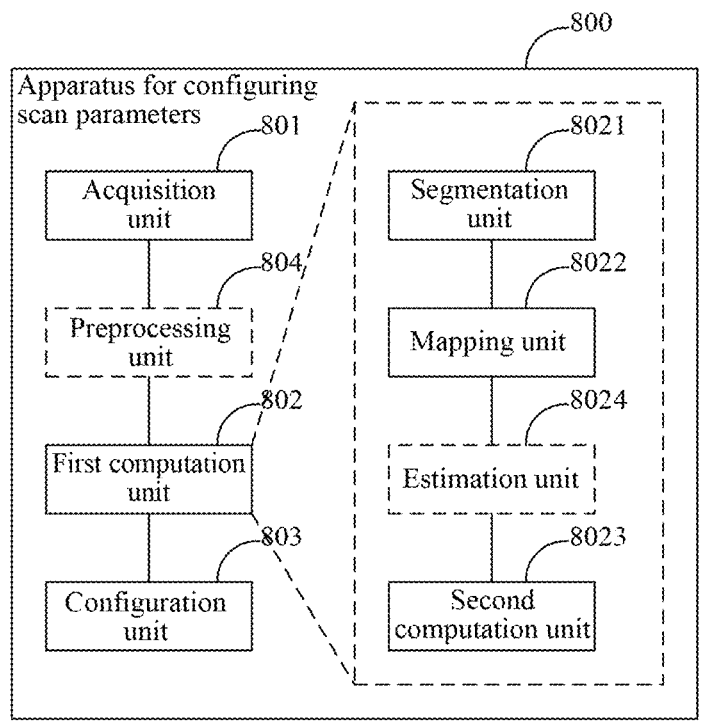
FIG. 8 is a schematic diagram of an apparatus for configuring scan parameters according to an embodiment of the present application.

FIG. 8 is a schematic diagram of the apparatus for configuring scan parameters according to this embodiment of the present application. As shown in FIG. 8, an apparatus 800 for configuring scan parameters includes: an acquisition unit 801 for acquiring an RGB image and a depth image of a scan object from a three-dimensional camera; a first computation unit 802 for computing physical parameters of the scan object according to the RGB image and the depth image of the scan object; and a configuration unit 803 for configuring, according to the physical parameters of the scan object, scan parameters for scanning the scan object.

In some embodiments, as shown in FIG. 8, the first computation unit 802 includes: a segmentation unit 8021 for segmenting the RGB image by means of a deep learning neural network to obtain two-dimensional profile information of the scan object; a mapping unit 8022 for mapping the two-dimensional profile information to the depth image so as to obtain upper surface information of the scan object; and a second computation unit 8023 for computing the physical parameters of the scan object according to the upper surface information of the scan object.

In some embodiments, as shown in FIG. 8, the first computation unit 802 further includes an estimation unit 8024 for estimating lower surface information of the scan object according to information of a supporting member supporting the scan object.

In the above embodiment, the second computation unit 8023 computes the physical parameters of the scan object according to the upper surface information and the lower surface information of the scan object.

In some embodiments, the information of the supporting member includes at least one of a shape, size, and configured height of the supporting member.

In some embodiments, as shown in FIG. 8, the apparatus 800 further includes a preprocessing unit 804 for performing preprocessing on the RBG image, the preprocessing including at least one of denoising, normalization, cropping, and scaling.

In the above embodiment, the first computation unit 802 computes the physical parameters of the scan object according to the preprocessed RBG image and the depth image of the scan object.

In some embodiments, the physical parameters of the scan object include at least one of the following: a length of the scan object; a thickness of the scan object; a width of the scan object; a volume of the scan object; and a weight of the scan object.

In some embodiments, the scan parameters include at least one of the following: a body mass index (BMI); a dosage and a flow rate of a contrast medium; a scan voltage and current; an indication of whether the scan object is beyond the scan field of vision; a medication administration range; a height of the supporting member; and an indication of whether the scan object is a special population.

In some embodiments, the scan object is the entire body or a portion of the scan object.

For the sake of simplicity, FIG. 8 only exemplarily illustrates connection relationships or signal directions between various components or modules, but it should be clear to a person skilled in the art that various related technologies such as bus connection can be used. The above components or modules can be implemented by hardware facilities such as a processor and a memory, and there are no restrictions thereto in the embodiments of the present application.

The above embodiments merely provide illustrative description of the embodiments of the present application. However, the present application is not limited thereto, and appropriate variations may be made on the basis of the above embodiments. For example, each of the above embodiments may be used independently, or one or more of the above embodiments may be combined.

According to this embodiment of the present application, the scan parameters for scanning the scan object can be automatically configured, so as to improve the efficiency and standardization of a scan process. Moreover, an appropriate configuration of the scan parameters can further avoid rescanning and poor-quality scout images resulting from manual errors.

Provided in an embodiment of the present application is an electronic device, including the apparatus 800 for configuring scan parameters according to the embodiment of the second aspect, the content of which is incorporated herein. The electronic device may be, for example, a computer, a server, a workstation, a laptop computer, a smart phone, etc., but this embodiment of the present application is not limited thereto.

Figure 9:
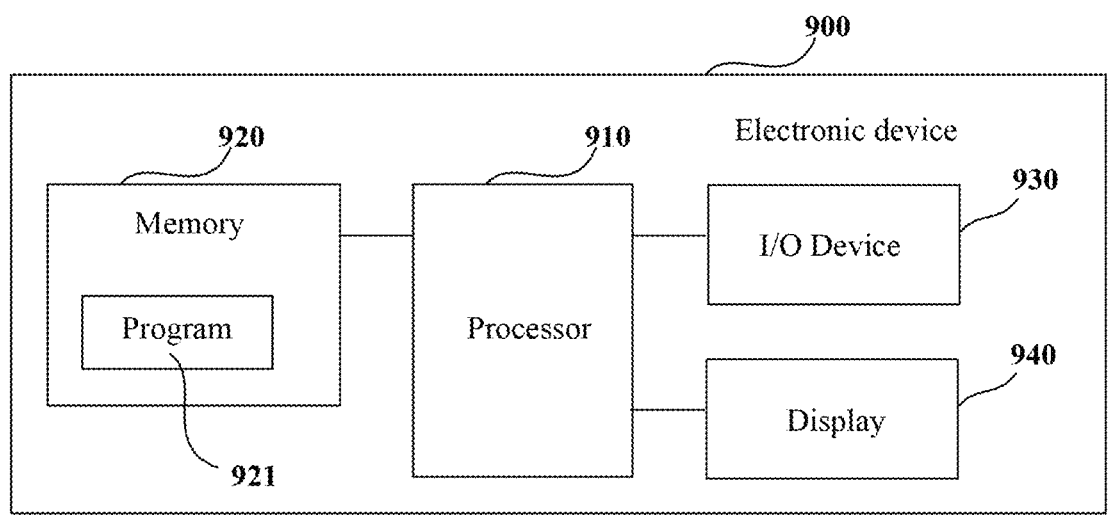
FIG. 9 is a schematic diagram of an electronic device according to an embodiment of the present application.

FIG. 9 is a schematic diagram of the electronic device according to this embodiment of the present application. As shown in FIG. 9, an electronic device 900 may include: at least one processor (e.g., a central processing unit (CPU)) 910 and at least one memory 920 coupled to the processor 910. The memory 920 can store various kinds of data, and can further store a program 921 for information processing, and execute the program 921 under the control of the processor 910.

In some embodiments, functions of the apparatus 800 for configuring scan parameters are integrated into the processor 910 for implementation. The processor 910 is configured to implement the method for configuring scan parameters as described in the embodiment of the first aspect.

In some embodiments, the apparatus 800 for configuring scan parameters and the processor 910 are configured separately. For example, the apparatus 800 for configuring scan parameters can be configured as a chip connected to the processor 910, and the functions of the apparatus 800 for configuring scan parameters can be realized by means of the control of the processor 910.

For example, the processor 910 is configured to control the following operations: acquiring an RGB image and a depth image of a scan object from a three-dimensional camera; computing physical parameters of the scan object according to the RGB image and the depth image of the scan object; and configuring, according to the physical parameters of the scan object, scan parameters for scanning the scan object.

In addition, as shown in FIG. 9, the electronic device 900 may further include: an input/output (I/O) device 930 and a display 940, etc., wherein functions of the above components are similar to those in the prior art, which are not be repeated herein. It should be noted that the electronic device 900 does not necessarily include all of the components shown in FIG. 9, and the electronic device 900 may further include components not shown in FIG. 9, for which reference may be made to the related art.

An embodiment of the present application further provides a computer-readable program. When the program is executed in an electronic device, the program enables a computer to execute, in the electronic device, the method for configuring scan parameters according to the embodiment of the first aspect.

An embodiment of the present application further provides a storage medium storing a computer-readable program. The computer-readable program enables a computer to execute, in an electronic device, the method for configuring scan parameters according to the embodiment of the first aspect.

The above apparatus and method of the present application can be implemented by hardware, or can be implemented by hardware in combination with software. The present application relates to such a computer-readable program that the program, when executed by a logical component, enables the logical component to implement the foregoing apparatus or constituent components, or enables the logical component to implement the various methods or steps described above. The present application also relates to a storage medium for storing the above program, such as a hard disk, a magnetic disk, an optical disk, a DVD, or a flash memory.

The method/apparatus described with reference to the embodiments of the present application may be directly embodied as hardware, a software module executed by a processor, or a combination thereof. For example, one or more of the functional block diagrams and/or one or more combinations of the functional block diagrams shown in the drawings may correspond to either respective software modules or respective hardware modules of a computer program flow. The software modules may respectively correspond to the steps shown in the figures. The hardware modules, for example, may be implemented by firming the software modules by using a field programmable gate array (FPGA).

The software modules may be located in a RAM, a flash memory, a ROM, an EPROM, an EEPROM, a register, a hard disk, a floppy disk, a CD-ROM, or any storage medium in other forms known in the art. One storage medium may be coupled to a processor, thereby enabling the processor to read information from the storage medium and to write information to the storage medium, or the storage medium may be a component of the processor. The processor and the storage medium may be located in an ASIC. The software module may be stored in a memory of a mobile terminal, or may be stored in a storage card that can be inserted into the mobile terminal. For example, if a device (e.g., a mobile terminal) adopts a large-capacity MEGA-SIM card or a large-capacity flash memory apparatus, the software module can be stored in the MEGA-SIM card or the large-capacity flash memory apparatus.

One or more of the functional blocks and/or one or more combinations of the functional blocks described in the drawings can be implemented as a general purpose processor, a digital signal processor (DSP), an application specific integrated circuit (ASIC), a field programmable gate array (FPGA) or other programmable logic devices, a discrete gate or transistor logic device, a discrete hardware component, or any appropriate combination thereof, for performing the functions described herein. One or more of the functional blocks and/or one or more combinations of the functional blocks described in the drawings can also be implemented as a combination of computation devices, e.g., a combination of a DSP and a microprocessor, a plurality of microprocessors, one or more microprocessors in communication with a DSP, or any other such configuration.

The present application has been described above with reference to the specific embodiments, but a person skilled in the art shall understand that the description is merely exemplary and does not limit the scope of protection of the present application. Those skilled in the art could make various variations and modifications to the present application according to the principle of the present application, and these variations and modifications are also within the scope of the present application.

What is claimed is:

1. An apparatus for configuring scan parameters, characterized by comprising:
   an acquisition unit for acquiring an RGB image and a depth image of a scan object from a three-dimensional camera;
   a first computation unit for computing physical parameters of the scan object according to the RGB image and the depth image of the scan object, wherein the first computation unit comprises:
   a segmentation unit for segmenting the RGB image by means of a deep learning neural network to obtain two-dimensional profile information of the scan object;
   a mapping unit for mapping the two-dimensional profile information to the depth image so as to obtain upper surface information of the scan object; and
   a second computation unit for computing physical parameters of the scan object according to the upper surface information of the scan object; and
   a configuration unit for configuring, according to the physical parameters of the scan object, scan parameters for scanning the scan object.

2. The apparatus according to claim 1, wherein the first computation unit further comprises
   an estimation unit for estimating lower surface information of the scan object according to information of a supporting member supporting the scan object; and
   the second computation unit computes the physical parameters of the scan object according to the upper surface information and the lower surface information of the scan object.

3. The apparatus according to claim 2, wherein the information of the supporting member comprises at least one of a shape, size, and configured height of the supporting member.

4. The apparatus according to claim 1, wherein the apparatus further comprises
   a preprocessing unit for performing preprocessing on the RBG image, the preprocessing comprising at least one of denoising, normalization, cropping, and scaling; and
   the first computation unit computes the physical parameters of the scan object according to the preprocessed RBG image and the depth image of the scan object.

5. The apparatus according to claim 1, wherein the physical parameters of the scan object comprise at least one of the following:
   a length of the scan object;
   a thickness of the scan object;
   a width of the scan object;
   a volume of the scan object; and
   a weight of the scan object.

6. The apparatus according to claim 1, wherein the scan parameters comprise at least one of the following:
   a body mass index (BMI);
   a dosage and a flow rate of a contrast medium;
   a scan voltage and current;
   an indication of whether the scan object is beyond the scan field of vision;
   a medication administration range;
   a height of the supporting member; and
   an indication of whether the scan object is a special population.

7. The apparatus according to claim 1, wherein the scan object is the entire body or a portion of the scan object.

8. A method for configuring scan parameters, characterized by comprising:
   acquiring an RGB image and a depth image of a scan object from a three-dimensional camera;
   computing physical parameters of the scan object according to the RGB image and the depth image of the scan object, wherein computing physical parameters of the scan object according to the RGB image and the depth image of the scan object includes:
   segmenting the RGB image by means of a deep learning neural network to obtain two-dimensional profile information of the scan object;
   mapping the two-dimensional profile information to the depth image so as to obtain upper surface information of the scan object; and
   computing physical parameters of the scan object according to the upper surface information of the scan object; and
   configuring, according to the physical parameters of the scan object, scan parameters for scanning the scan object.

9. The method according to claim 8, wherein the step of computing physical parameters of the scan object according to the RGB image and the depth image of the scan object further includes:
   estimating lower surface information of the scan object according to information of a supporting member supporting the scan object; and
   computing physical parameters of the scan object according to the upper surface information and the lower surface information of the scan object.

10. The method according to claim 9, wherein the information of the supporting member includes at least one of a shape, size, and configured height of the supporting member.

11. The method according to claim 8, further comprising:
    performing preprocessing on the RBG image, the preprocessing including at least one of denoising, normalization, cropping, and scaling; and
    computing the physical parameters of the scan object according to the preprocessed RBG image and the depth image of the scan object.

12. The method according to claim 8, wherein the physical parameters of the scan object include at least one of the following:
    a length of the scan object;
    a thickness of the scan object;
    a width of the scan object;
    a volume of the scan object; and
    a weight of the scan object.

13. The method according to claim 8, wherein the scan parameters include at least one of the following:
    a body mass index (BMI);
    a dosage and a flow rate of a contrast medium;
    a scan voltage and current;
    an indication of whether the scan object is beyond the scan field of vision;
    a medication administration range;
    a height of the supporting member; and
    an indication of whether the scan object is a special population.

14. The method according to claim 8, wherein the scan object is the entire body or a portion of the scan object.

* * * * *